(12) United States Patent
Fouts et al.

(10) Patent No.: US 10,544,172 B2
(45) Date of Patent: Jan. 28, 2020

(54) PHOSPHATE COMPOSITION

(71) Applicant: VANTAGE SPECIALTIES, INC., Warren, NJ (US)

(72) Inventors: Christine Fouts, East Palatka, FL (US); Jay Wang, Naperville, IL (US)

(73) Assignee: Vantage Specialties, Inc., Warren, NJ (US)

( * ) Notice: Subject to any disclaimer, the term of this patent is extended or adjusted under 35 U.S.C. 154(b) by 0 days.

(21) Appl. No.: 15/837,637

(22) Filed: Dec. 11, 2017

(65) Prior Publication Data

US 2018/0298041 A1    Oct. 18, 2018

Related U.S. Application Data

(63) Continuation of application No. 14/699,530, filed on Apr. 29, 2015, now abandoned.

(60) Provisional application No. 61/986,576, filed on Apr. 30, 2014.

(51) Int. Cl.
| | |
|---|---|
| *C10M 159/12* | (2006.01) |
| *C07F 9/09* | (2006.01) |
| *C07F 9/10* | (2006.01) |
| *C10M 141/00* | (2006.01) |
| *C10M 141/06* | (2006.01) |
| *C07F 9/6574* | (2006.01) |
| *C07F 9/141* | (2006.01) |
| *C10M 141/10* | (2006.01) |

(52) U.S. Cl.
CPC ............... *C07F 9/091* (2013.01); *C07F 9/09* (2013.01); *C07F 9/10* (2013.01); *C07F 9/141* (2013.01); *C07F 9/65742* (2013.01); *C10M 141/00* (2013.01); *C10M 141/06* (2013.01); *C10M 141/10* (2013.01); *C10M 159/12* (2013.01)

(58) Field of Classification Search
CPC ........ C07F 9/091; C07F 9/65742; C07F 9/10; C07F 9/09; C07F 9/141; C10M 141/10; C10M 141/00; C10M 141/06; C10M 159/12
See application file for complete search history.

(56) References Cited

U.S. PATENT DOCUMENTS 5,851,962 A * 12/1998 Kaga .................... C10M 141/02
508/162

FOREIGN PATENT DOCUMENTS

CN           102140380 A  *  8/2011

* cited by examiner

*Primary Examiner* — Taiwo Oladapo
(74) *Attorney, Agent, or Firm* — Fox Rothschild LLP

(57) ABSTRACT

A process for the preparation of a composition comprising amine-containing phosphate glycerides including: phosphorylating a solution which comprises mixed glycerides that contain fatty acid portions and an amine under conditions which are substantially water-free and under which said phosphorous pentoxide reacts with reactive constituents in said solution to form said amine-containing phosphate glycerides and a lubricating composition comprising a lubricant, the aforesaid composition in an amount which improves the properties of the lubricating composition, and optionally one or more other constituents which improve the properties of the lubricating composition.

27 Claims, No Drawings

PHOSPHATE COMPOSITION

CROSS-REFERENCE TO RELATED APPLICATION

The present application is a continuation of U.S. application Ser. No. 14/699,530, filed Apr. 29, 2015, which claims priority to U.S. Provisional Application Ser. No. 61/986,576, filed Apr. 30, 2014.

FIELD OF THE INVENTION

The present invention relates to the provision of phosphate esters. More particularly, the invention relates to amine-containing phosphate compositions.

The present invention can be used to particular advantage in various applications, including, for example, as an additive in lubricating compositions. The lubricating compositions which contain the additive of the present invention can be of various types, for example, those designed for use as engine oils, hydraulic fluids, and metal-working fluids and in applications which are benefitted by the use of grease.

For use as an additive in lubricating compositions, the composition of the present invention functions to improve the overall properties thereof, including performance properties, for example, anti-wear properties; in addition, they function excellently as an extreme-pressure additive. As to physical/chemical properties of compositions which contain the additive hereof, they exhibit stability, resist demulsification and have viscosity properties within desired ranges. The Example section hereof provides evidence of the additive hereof to function in a synergistic manner.

SUMMARY OF THE INVENTION

The present invention provides a process for the preparation of a composition comprising amine-containing phosphate glycerides which involves: (a) providing or preparing a solution which comprises mixed glycerides which contain fatty acid portions and an amine (hereafter "Solution A"); (b) providing or preparing a reactive solution (hereafter "Solution B") which comprises phosphorous pentoxide and Solution A; and (c) phosphorylating a mixture of said Solutions A and B under conditions which are substantially water-free and under which said phosphorous pentoxide reacts with reactive constituents in Solution A to form said amine-containing phosphate glycerides.

In preferred form, the source of the mixed glycerides of said Solution A includes the product of the transesterification of a triglyceride with glycerol; and most preferably the source of the triglyceride includes soybean oil. In addition, the mixed glycerides of Solution A include monoesters and diesters of glycerol in which the carbon chain length of the fatty acid of said portions is a short chain, medium chain and/or a long chain and the fatty acid of said portions is a saturated fatty acid and/or a mono- or a poly-unsaturated fatty acid and wherein said portions comprise the same or a different fatty acid.

DETAILED DESCRIPTION OF THE INVENTION

The process of the present invention includes providing or forming a solution comprising mixed glycerides and an amine and subjecting the solution to phosphorylation.

The term "mixed glycerides" as used herein means the liquid product obtained by transesterifying a triglyceride with glycerol which is a liquid polyol known also as "1,2,3-propanetriol" and "glycerine". Triglycerides are triesters which comprise a fatty acid portion and an alcohol portion. The three fatty acid portions of the triester can be derived from any suitable fatty acid, including, for example, a fatty acid having a chain length as follows: (A) a short chain (fewer than six carbon atoms); (B) a medium chain (six to 12 carbon atoms); and (C) a long chain (13 or more carbon atoms). The fatty acid portion can be derived from a saturated fatty acid, or a mono- or a poly-unsaturated fatty acid. The acid portion can comprise the same or different fatty acids.

Preferred triglycerides have fatty acid portions of both saturated and unsaturated acids and of medium and long chain acids.

In preferred form, a natural-occurring product, most preferably, soybean oil is the source of the triglyceride(s) which are transesterified with glycerol. The triglycerides can be derived from other sources also. For example, they can be synthetically-prepared by reacting one or more suitable fatty acids with glycerol.

In its basic form, transesterification involves the reaction of: (A) a monohydric alcohol (ROH) with (B) a "simple" ester that is formed by reacting a monohydric alcohol (R'OH) with a monocarboxylic acid, for example, a fatty acid. This basic reaction produces a product which consists of: (A) a "new" monohydric alcohol in which its OH group is bonded to the R' group of the ester reactant; and (B) a "new" ester which includes the R group of the ROH reactant.

Compared to such a basic transesterfication, as described above, the transesterification that is used in the process of the present invention is more complicated.

For example, the reactants include a trihydric alcohol (the glycerol) and triester in the form of a triglyceride which includes residues of three acids which may be the same, but in preferred form are different. Also, a variety of numerous compounds can be produced. Some exemplary compounds are α-monoesters and α- and β-diesters which are formed from the glycerol and the triglyceride reactions and which have different carbon chain lengths, for example, from C8 to C22.

Consider also that the triglycerides in soybean oil include esters having fatty acid portions which can be saturated, mono-unsaturated, and polyunsaturated, the last mentioned comprising about 55 wt. % of the total of the fatty acid portion of the triglyceride esters. Saturated fatty acid portions of the triglycerides comprise about 15 wt. % of the acids and include stearic and palmitic acid (about 5% and about 10% respectively). The unsaturated fatty acid portions of the triglycerides comprise the major proportion thereof (about 80 wt. %) and include, for example, oleic acid (monounsaturated—about 25 wt. %), whereas the polyunsaturated fatty acid portion comprises about 60 wt. % and includes linolenic acid (tri-unsaturated; about 10 wt. %) and linoleic acid (about 50 wt. %). This compositional information regarding the distribution of fatty acids in soybean oil can be found in numerous publications.

Accordingly, the product of the transesterifacation of soybean oil includes monoglycerides, and diglycerides of fatty acids, for example, stearic, palmitic, oleic, linolenic, and linoleic.

The transesterification involves the use of liquid reactants; it is conducted under conditions that produce a product which includes mixed glycerides in liquid form. Exemplary conditions of reaction include use of: (A) atmospheric pressure; (B) a temperature of about 350 to about 400° F.;

and (C) a time of about 4 to about 8 hours. The molar ratio of the triglyceride/glycerol reactants will have an effect on the weight ratio of the mono-/di-glycerides present in the product of the transesterification. For example, 10 wt. % glycerol in the system will yield about 15% monoglycerides. As exemplified in Examples set forth below, it is preferred that an appropriate catalyst be used in the transesterification, for example, KOH, K2CO3 and H2SO4.

The process of the present invention includes also the provision of or the formation of a solution comprising mixed glycerides and an amine. One of the reasons for use of the amine is to control the acid value (or AV) of the final phosphorylated product; during phosphorylation, the AV of the reaction mixture can decrease to an extent that the use of the product as an additive in a lubricating composition can affect adversely the metals being lubricated. It is preferred that the final phosphorylated product have an AV within a range of about 60 to about 90. The presence of the amine contributes also to antiwear properties of metals being lubricated by improving film-forming on the surfaces of metals relative to that of phosphates alone.

Amines which are included in the solution of mixed glycerides are primary or secondary amines, for example: (A) a secondary amine having a short to medium chain length (6 to 12 C atoms); or (B) a primary amine having a long chain length (18 to 21 or more C atoms). Examples of specific amines that can be used are oleylamine, ethyhexylamine, and ethoxylated oleylamine. Bis(2-ethylhexyl) amine, a liquid secondary amine, has been used to particularly good advantage.

An ethoxylated amine can be included also in the solution of mixed glycerides with or without an amine of the type described above. The (ETO) should be a liquid at room temperature; examples of ETO are within the scope of the Formula 1 below in which R is hydrocarbon chain with a C number between 6-22.

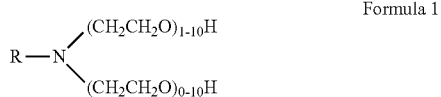

Formula 1

A preferred ETO is the secondary amine, oleylamine, and particularly one in which each of the ethoxy groups numbers 2.

The form of the final product can be influenced by the amine or ETO used. For example, final products which are in liquid form can be formulated from liquid secondary amines which have a short to medium chain (6 to 12 carbon atoms); they are well suited as additives in lubricating compositions which are in liquid form. On the other hand, final products which are in soft paste form can be formulated from liquid primary amines which have a long chain (18 to 21 or more carbon atoms); they are well suited as additives in a lubricating composition which is a grease.

The amount of amine or ETO (collectively for convenience, hereafter "amine" unless indicated otherwise) included in the mixed glycerides should be an amount sufficient to lower the acid value, for example, to no less than about 20. Preferably, the amount of the amine should comprise about 45 to about 50 wt % of the composition comprising the product of the transesterification, the amine, and the phosphorylating agent described below.

In accordance with the present invention, the mixed glycerides/amine solution is subjected to phosphorylation, a known type of reaction. The term "phosphorylation" is used herein in the broad sense to include the addition of a phosphate group to an organic molecule. In the present development, the source of the organic molecule is a product(s) of the aforementioned TRESTF, for example, various glycerides, as described (any other compounds). The phosphorylation can be effected, for example, using phosphorous pentoxide (P2O5 which is known also as diphosphorous pentoxide, phosphorous (V) oxide, and phosphoric anhydride).

The amount of phosphorylating agent used in the phosphorylation should be sufficient to maximize anti-wear or extreme pressure properties. In preferred form, the amount of the agent should comprise about 10 to about 20 wt. % of the composition comprising the mixed glycerides (product of the transesterification), the amine, and the phosphorylating agent. The mixed glycerides comprise about 30 to about 50 wt. %, preferably about 30 to about 45 wt. % of the composition, and, as mentioned above, the amine comprises about 45 to about 50 wt. % of the composition.

The phosphorylation should be carried out under conditions which minimize moisture content. The phrase "under conditions which are substantially water-free" as used herein in the context of the phosphorylation means that the water content of the conditions is free of water or has a water content of no greater than about 0.2 wt. %. Other conditions which are exemplary of the phosphorylation include the use of: (A) atmospheric pressure; (B) a temperature ranging from room temperature to about 380° F.; and (C) a time of about 4 to about 6 hours.

For convenience, the product of the reaction of the phosphorylating agent and of the trensesterification is referred to herein as "phosphate glycerides". It is believed, that the amine forms a salt or complex with the phosphate glycerides. Accordingly, the preferred amine and/or ETO for use in the practice of the present invention is one that forms a salt/complex with the phosphate glycerides. It is preferred also that the amine be present in the solution of mixed glycerides before phosphorylation. If the phosphorylating agent reacts with the mixed glycerides in the absence of the amine, it is believed that steric hindrance impedes the association of the amine (salt/complex formation) with the phosphate glycerides. For convenience, the final product of the phosphorylation is referred to as "amine salt/complex of phosphate glycerides" or as "amine-containing phosphate glycerides".

The product of the present invention can be used as an additive in a lubricating composition. Such compositions function, for example, to reduce friction between moving parts, typically metal parts, to separate moving parts by forming a thin layer between the surfaces of the parts, and to transfer heat or contaminates away from the surfaces being lubricated.

Typically, the major component of a lubricating composition is a lubricant, referred to conventionally as a "base oil" which is admixed with one or more additives which improve the properties of the lubricating composition, for example, that impart to or improve "performance" properties of the lubricating composition.

Examples of base oils include: mineral oils derived from crude oil, for example, paraffinic, naphthenic, and aromatic compounds; vegetable oils, for example, canola oil, palm oil, and Tall oil; and synthetic oils, for example, alkylated naphthalenes and silicate esters.

Examples of classes of additives for use in a lubricating composition include compounds which function as: antioxidants; detergents; anti-wear agents; metal deactivators; corrosion-inhibitors; friction modifiers; extreme pressure agents; anti-foaming agents; viscosity index improvers; and demulsifying agents.

The additive of the present invention can be used in any lubricating composition in which it is compatible with the lubricant and other ingredients that comprise the composition.

For example, the additive hereof can be used in engine oils which are designed to protect metal parts being lubricated against mechanical wear (extreme-pressure and wear protection) and corrosion. An exemplary lubricating composition for use as an engine oil comprises, a base oil, a product (additive) of the present invention, and one or more other additives and in which the product of the present invention comprises, for example, about 0.5 to about 5% by weight of the total weight of the composition.

Examples of base oils include mineral oils, poly-alpha-olefins (PAOs), and esters and mixtures thereof, for example, amounts which comprise about 5 to about 20 wt. % or about 70 to about 80 wt. % of the lubricating composition. Examples of other additives for use in the composition include antioxidants, anti-foaming agents, metal passivators, rust-inhibitors, dispersants, detergents, solid lubricants, viscosity index improvers, pour-point depressants, additional extreme-pressure additives, anti-wear additives, and additives which reduce the coefficient of friction (friction modifiers). Additives generally comprise from about 0.01 to about 20% by weight of a lubricating composition, including a composition suitable for use as engine oil which typically is used to lubricate internal combustion engines, for example, in motor vehicles fitted, for example, with engines of the Otto, Diesel, two-stroke, Wankel or orbital type.

For use in an engine oil, the additive can be added to a base oil in which it is readily soluble. It is also possible to prepare a so-called master batch of a plurality of additives which can be diluted with the base oil until the desired concentrations of the additives are achieved. Also the additive of the present invention may be introduced as part of so-called "additive package".

Products of the present invention can be used also as additives in lubricating compositions that are suitable for use in hydraulic fluids and gear oil; their use includes the protection of metal parts to be lubricated against mechanical wear. Accordingly, the present invention can be used to improve the service properties of hydraulic fluids and gear oils. For use in such applications, the additive of the present invention can comprise, for example, about 0.5 to about 2% by weight of the lubricating composition. Use of the additive of the present invention can be accompanied by the use of other additives which provide hydraulic fluids with optimum performance characteristics, for example, pumpability, compressibility, wear-resistance, both oxidation and thermal stabilities, filterability, resistance to demulsifying, foam-resistance, rust- and corrosion-resistance, hydrolytic stability, and seal compatibility.

The product of the present invention can be used also as an additive in a lubricating composition suitable for use as a metal-working fluid. The use of such a composition helps to protect the metal parts to be lubricated against mechanical wear under normal- and extreme-pressure operations and to help also in maintaining a constant temperature in an application which involves the use of metal parts, tools, and machine operations. The additive of the present invention can comprise, for example, about 2 to about 5% by weight of a lubricating composition which is suitable for use as a metal-working fluid and which generally contains other additives, for example, those identified above. The additives, including the additive of the present invention, provide metal working fluids with optimum performance characteristics, excellent lubricity, rust control, long sump life, and low foam.

Products within the scope of the present invention can be used also as an additive in a lubricating composition which is known as "grease". In one sense, grease can be described as a thickened base oil, for example, a semisolid lubricant; nevertheless, the term is applied also to high viscosity liquids or soft solids that have lubricating properties.

Examples of base oils that can be used in greases are mineral and synthetic oils to which a product of the present invention can be introduced as an additive in any suitable way. The additive is typically compatible with popularly used base oils and conventional thickening agents which are used to convert the base oil into a grease. For most applications, it is believed that the use of the additive hereof in an amount of about 1 to about 4% by weight (based on the total weight of the grease) will be sufficient. The grease composition typically contains other additives, for example, metallic soaps or other thickeners, antioxidants, rust- and corrosion-inhibitors, anti-wear and extreme-pressure additives, and friction modifiers.

It should be appreciated that products of the present invention can be used as an effective additive in a wide variety of applications in which they function to improve the properties of the lubricating composition to which they have been added. Examples of their use have been described above and the Example section hereof contains additional information respecting their effective use.

There follows additional information concerning preferred embodiments of their use. They can be either used as anti-wear additives (AW) or extreme pressure additives (EP) based on the ratio of amine, products of TRESTF, and phosphorylation. It is recommended that an additive which imparts to the lubricating composition particularly good anti-wear properties comprise: about 30 to about 45 wt. % of the products of TRESTF; about 45 to about 50 wt. % of amine; and about 5 to about 10 wt. % of said phosphorous pentoxide. For particularly good extreme-pressure properties, it is recommended that the additive comprise about 43 to about 48 wt. % amine, about 40 to about 43 wt. % products of TRESTF, and about 9 to about 18 wt. % said phosphorous pentoxide.

EXAMPLES

The following are examples of additives according to the present invention and of their evaluation of use in lubricating compositions in applications involving anti-wear and extreme pressure. Unless stated otherwise, "wt. %" means % by weight based on the total weight of the stated ingredients. Example Nos. 1 and 2 below exemplify respectively the use of mixed glycerides prepared from soy bean oil by transesterification.

Example No. 1

This example describes the preparation of a composition of the present invention by: (a) forming a product from the transesterification (TRESTF) of (i) soybean oil and (ii) glycerol; (b) adding to the aforementioned product Bis(2-ethylhexyl) amine to form a solution of the ingredients; and (c) reacting ingredients of the solution with phosphorous pentoxide.

Product of Transesterification

A solution containing 2013 grams of soybean oil, 103 grams of glycerol, and 8 grams of potassium carbonate (catalyst) was prepared by heating the liquid ingredients at room temperature and atmospheric pressure. The solution was heated thereafter for one hour at 440° F. (a temperature which is below the burning temperature of soy bean oil) with nitrogen sparging and agitation to form a second solution comprising alpha-monoglyceride (10 to 14 wt. %), diglycerides (90 to 96 wt. %), and a trace amount of free glycerol. The second solution was filtered through a 100 micron filter; the filtrate was a solution referred to hereafter as "the mixed glycerides".

Phosphorylation of the Mixed Glycerides in Presence of an Amine

One hundred thirty-five grams of commercial grade Bis (2-ethylhexyl) amine and 135 grams of the aforementioned mixed glycerides were mixed at atmospheric pressure and at room temperature to form a solution (hereafter "Solution A"). Twenty-nine grams of commercial phosphorus pentoxide (P2O5) were added to Solution A at room temperature and atmospheric pressure with agitation in the absence of water to form a reactive solution (hereafter "Solution B"). The temperature of Solution B rose to between about 50° F. to about 100° F. due to the reaction between the P2O5 and glycerides and residual moisture in the surrounding environment. Solution B was then heated to 380° F. under nitrogen sparging and agitation for about 4 hours. The reaction was considered complete as verified by refractive index of 1.40-1.50.

The product of the reaction was filtered through a 100 micron bag filter and there was recovered a viscous brown liquid containing the additive of the present invention. The physical properties of the liquid (hereinafter "phosphate-1") were: (a) acid value—40.0 to 90.0; (b) % water—<0.02%; (c) % N content—2.00 to 3.00%; and (d) % phosphorous content—4.2 to 4.5%.

The following lubricating composition containing phosphate-1 was prepared.

| Lubricating Composition A | |
| --- | --- |
| Ingredient | Amount - %* |
| lubricant (poly alpha olefin (PAO)) | 99-99.5 |
| phosphate-1 | 0.5-1.0 |

Composition A above had the following properties: (a) density—0.84 g/cm3; (b) viscosity @40° C.—223.9; (c) viscosity index—182. Comparing properties of Composition A with a commercially available lubricating composition that contains 0.5% Irgalube 349, the anti-wear properties of Composition A herein are in-line with those of the "IRGALUBE 349" compositions; however, Composition A hereof has superior properties in that it has a relatively high flash point (274° C.), low TAN (0.458), and resists demulsification.

Example No. 2

A phosphate composition differing from phosphate-1 of Example No. 1 and referred to hereafter as "phosphate-2" was prepared as follows.

The process used to prepare phosphate-2 included, like Example No. 1, the use Bis(2-ethylhexyl) amine and P2O5, but in different amounts as indicated hereafter.

Commercial grade Bis(2-ethylhexyl) amine in an amount of 141.2 grams and 105.9 grams of the aforementioned mixed glycerides (Example No. 1) were mixed at atmospheric pressure and at room temperature to form a solution (hereafter "Solution A-2"). Fifty-three grams of commercial phosphorus pentoxide (P2O5) were added to Solution A-2 at room temperature and atmospheric pressure with agitation in the absence of water) to form Solution B-2. The balance of this description of the preparation of phosphate-2 is like that of Example No. 1. Thus, the temperature of Solution B-2 rose to between about 50° F. to about 100° F. due to the reaction between the P2O5 and the glycerides and residual moisture in the surrounding environment. Solution B-2 was then heated to 380° F. under nitrogen sparging and agitation for about 4 hours. The reaction was considered complete as verified by refractions index and 1.40-1.50.

The product of the reaction was filtered through a 100 micron bag filter and there was recovered a viscous brown liquid containing the additive of the present invention. The physical properties of the liquid phosphates (hereinafter "phosphate-2") were: (a) acid value—40.0 to 70.0; (b) % water—<0.02%; (c) % N content—2.00 to 3.00%; and (d) % phosphorous content—7.3 to 7.8%.

The following lubricating composition containing phosphate-2 was prepared.

| Lubricating Composition A-2 | |
| --- | --- |
| Ingredient | Amount - % |
| lubricant (poly alpha olefin (PAO)) | 99-99.5 |
| phosphate-2 | 0.5-1.0 |

Composition A-2 above had the following properties: (a) density—0.84 g/cm3; (b) viscosity @40° C.—232.5; (c) viscosity index—178. The comparison described above in connection with Lubricating Composition A, was made to compare the properties of Composition A-2 with a commercially available lubricating composition that contains 0.5 wt. % of the BASF trademarked product IRGALUBE 349. The anti-wear properties of Composition A-2 herein are in-line with those of the "IRGALUBE 349" composition; however, Composition A-2 herein has superior properties such as a high flash point (283° C.), low TAN (0.492), and an ability to resist demulsification. Lubricating Composition A-2 has also improved properties in tests relating to seizure load and 4-ball scar width relative to those associated with the use of the "IRGALUBE 349" composition.

Other Comparative Tests

The use of phosphate-2 (which contained 7.6 wt %, of phosphorous) as an extreme-pressure additive in lubricating compositions was compared with the use of commercially available extreme-pressure additives in such composition. The lubricant (base oil) used in the lubricating compositions was canola oil and the commercially available extreme-pressure additives were chlorinated paraffin (Cl-paraffin) and triphenylphosphorothionate (TPPT). Table 1 below identifies the tests to which the composition were subjected and the results of the testing.

TABLE 1

| Canola Oil | 4-Ball | | Timken | Pin & Vee Block | |
|---|---|---|---|---|---|
| Lubricating Composition Wt % Additives | weld point | low-wear | load capacity (pass) | Teeth Counts | Torque (lb/in2) |
| 20% Cl-paraffin | 800 kg | 80 kg | 70 lb (P)/75 lb (F) | 1301 | 73.4 lbs |
| 50% Cl-paraffin | 800 kg | 100 kg | Not available (N/A) | 1293 | 80.6 lbs |
| 10% TPPT | 315 kg | 73 kg | (N/A) | N/A | N/A |
| 5% phosphate-2 | 800 kg | 100 kg | 70 lb (P)/75 lb (F) | 900 | >129 lbs |
| 10% phosphate-2 | 800 kg | 100 kg | 75 lb (P)/80 lb (F) | 890 | >129 lbs |
| blend 5% of Cl-paraffin and 5% phosphate-2 | 800 kg | 100 kg | N/A | 1226 | 55.1 lbs |

A review of the test results in Table 1 shows the surprising synergistic effect that is associated with the use of the phosphate-2 additive of the present invention. Note that the blend of 5% phosphate-2 and 5% chlorinated paraffin provides the lubricating composition with outstanding performance compared to the use of 50% of chlorinated paraffin.

Attached hereto is Appendix A which shows structurally the sequences of reactions involved in the preparation of an exemplary product of the present invention.

The invention claimed is:

1. A process for the preparation of a composition comprising amine-containing phosphate glycerides including providing a solution which comprises the following ingredients: (a) mixed glycerides which contain fatty acid portions and (b) an amine, said ingredients not being reactable with each other (hereafter "Solution A"); phosphorylating with phosphorous pentoxide said Solution A under reactive conditions which are substantially water-free to form said amine-containing phosphate glycerides.

2. A process according to claim 1, wherein the source of the mixed glycerides of said Solution A includes the product of the transesterification of a triglyceride with glycerol.

3. A process according to claim 2, wherein the source of said triglycerides includes soybean oil.

4. A process according to claim 2, wherein the source of said triglycerides includes a synthetically prepared mixture thereof obtained by reacting one or more suitable fatty acids with glycerol.

5. A process according to claim 1, wherein the mixed glycerides of Solution A include monoesters and diesters of glycerol in which the carbon chain length of the fatty acid of said portions is a short chain, a medium chain and/or a long chain and the fatty acid of said portions is a saturated fatty acid and/or a mono- or a poly-unsaturated fatty acid and wherein said portions comprise the same or a different fatty acid.

6. A process according to claim 4, wherein said fatty acid includes either stearic, palmitic, oleic, linolenic, or linoleic acid or said fatty acids include a mixture of two or more of the aforementioned acids.

7. A process according to claim 1, wherein the amine of Solution A is a primary or secondary amine wherein said secondary amine has a short to medium chain length (6 to 12 C atoms) and said primary amine has a long chain length (about 18 to about 21 or more C atoms).

8. A process according to claim 7, wherein the amine is selected from the group consisting of oleylamine, ethyhexylamine, and Bis(2-ethylhexyl) amine.

9. A process according to claim 1, in which the amine of Solution A is an ethoxylated amine (ETO) within the scope of Formula 1 below in which R is a hydrocarbon chain with a C number between about 6 to about 22.

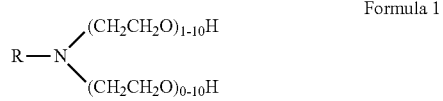

Formula 1

10. A process according to claim 9, wherein the amount of ETO comprising Solution A is about 45 to about 50 wt % based on the amount of the mixed glycerides and phosphorous pentoxide.

11. A process according to claim 1, wherein said phosphorylating conditions include about 10 wt. % to about 20 wt. % of phosphorous pentoxide based on the weight of Solution A.

12. A process according to claim 1, wherein said phosphorylating conditions include a water content that is no greater than about 0.2 wt. %.

13. A process according to claim 1, wherein, in the product of the phosphorylation, the amine is associated with the phosphate glycerides in the form of a salt or complex.

14. A product comprising amine-containing phosphate glycerides formed by the process of claim 1 (hereafter "additive").

15. A lubricating composition comprising:
(A) a lubricant;
(B) additive of claim 14 which improves the properties of the lubricating composition; and optionally
(C) one or more other additives which improve the properties of the lubricating composition.

16. A lubricating composition of claim 15, which is effective for use as an engine oil or as a hydraulic fluid or as a gear oil or as a metal-working fluid, or which is in the form of a grease.

17. A lubricating composition of claim 15, in which the lubricant is one or more of (A) mineral oils derived from crude oil and selected from the group consisting of paraffinic, naphthenic, and aromatic compounds; (B) vegetable oils selected from the group consisting of canola oil, palm oil, and Tall oil; and (C) synthetic oils selected from the group consisting of alkylated naphthalenes and silicate esters.

18. A lubricating composition of claim 15, containing an additive of claim 15, and one or more other additives which function as an antioxidant; a detergent; an anti-wear agent; a metal deactivator; a corrosion-inhibitor; a friction modifier; an extreme-pressure agent; an anti-foaming agent; a viscosity index improver; and a demulsifying agent.

19. A composition of claim 15, comprising:
  (A) about 70 to about 80 wt. % of said lubricant;
  (B) about 0.5 to about 5 wt. % of said additive of (B); and
  (C) about 5 to about 20 wt. % of one or more said other additives of (C).

20. A product prepared by the process of claim 2, and comprising: about 30 to about 50 wt. % of the product of said transesterification; about 45 to about 50 wt. % of said amine; and about 10 to about 20 wt. % of said phosphorous pentoxide.

21. A product prepared by the process of claim 2, and comprising: about 43 to about 48 wt. % of said amine; about 30 to about 45 wt. % of the product of said transesterification; and about 9 to about 18 wt. % said phosphorous pentoxide.

22. A process for the preparation of a composition comprising amine-containing phosphate glycerides including: (i) providing a solution which comprises mixed glycerides that contain fatty acid portions and an amine in unreactive form, said amine being selected from the group consisting of oleylamine, ethyhexylamine, Bis(2-ethylhexyl) amine, and an ethoxylated amine, including ethoxylated oleylamine (hereafter "Solution A"); (ii) providing a reactive solution (hereafter "Solution B") which comprises phosphorous pentoxide and Solution A; (iii) combining Solution (A) and Solution (B); and (iv) subjecting the combined solutions to phosphorylating conditions which are substantially water-free and under which said phosphorous pentoxide reacts with said mixed glycerides and said amine to form said amine-containing phosphate glycerides.

23. A composition comprising amine-containing phosphate glycerides prepared by the process of claim 22.

24. A process according to claim 22 wherein the mixed glycerides include monoester and diesters of glycerol in which the carbon chain length of the fatty acid of said portions is a short chain, a medium chain and/or a long chain and the fatty acid of said portions is a saturated fatty acid and/or a mono- or a poly-unsaturated fatty acid and wherein said portions comprise the same or a different fatty acid.

25. A composition which functions as an additive in a lubricating composition and which comprises amine-containing phosphate glycerides prepared by the process of claim 24.

26. A lubricating composition which comprises the composition of claim 25 as an additive that improves the properties of the lubricating composition and optionally one or more other additives that improve the properties of the lubricating composition.

27. A composition of claim 15, comprising:
  (A) about 5 to about 20 wt. % of said lubricant;
  (B) about 0.5 to about 5 wt. % of said additive of (B); and
  (C) about 5 to about 20 wt. % of one or more said other additives of (C).

* * * * *